United States Patent [19]

Matthews et al.

[11] Patent Number: 4,851,195
[45] Date of Patent: Jul. 25, 1989

[54] CARBON DIOXIDE SENSOR

[75] Inventors: Richard S. Matthews, North Storrington; Frederick E. Witherell, Jr., East Lyme, both of Conn.

[73] Assignee: Pfizer Hospital Products Group, Inc., New York, N.Y.

[21] Appl. No.: 86,423

[22] Filed: Aug. 17, 1987

[51] Int. Cl.$^4$ ............................................. G01N 21/77
[52] U.S. Cl. ....................................... 422/68; 422/55; 422/58; 436/68; 436/133; 436/163; 436/167; 436/172; 436/178; 356/39; 250/459.1; 250/461.1; 128/634
[58] Field of Search .................... 422/55, 58, 59, 68; 435/807, 808; 436/68, 133, 163, 164, 167, 172, 178; 128/632–634, 653, 666; 204/400, 415, 433; 250/373, 458.1, 459.1, 461.1; 356/39, 40, 402, 441

[56] References Cited

U.S. PATENT DOCUMENTS

| Re. 31,879 | 5/1985 | Lubbers et al. | 436/133 |
|---|---|---|---|
| 3,865,548 | 2/1975 | Padawer | 436/133 X |
| 4,200,110 | 4/1980 | Petersen et al. | 128/634 |
| 4,495,293 | 1/1985 | Shaffar | 436/172 |
| 4,557,900 | 12/1985 | Heitzmann | 422/55 |

OTHER PUBLICATIONS

Hirshfeld, "Reabsorption Sensing in Fluorescence Spectroscopy", UCRL Abstract No. 89736 ABST, published by Pittsberg Conference on Scientific Instrumentation, Mar. 1984.
Gehrich et al., "Optical Fluorescence and its Application to an Intravascular Blood Gas Monitoring System", IEEE Transactions on Biomedical Engineering, vol. BME-33, No. 2, 2/86.
Seitz, "Chemical Sensors Based on Fiber Optics", Analytical Chemistry, vol. 56, pp. 16a–34a, 1984.
Udenfreund, "Fluorescence Assay in Biology and Medicine" (1962) pp. 108–109.
S. M. Angel, "Optrodes: Chemically Selective Fiber Optic Sensors", Spectroscopy, Apr. 1987, pp. 38–47.
Forster, "Intermolecular Energy Transfer and Fluorescence, Annaten der Physik" (1948) pp. 55–75.

Primary Examiner—Robert J. Hill, Jr.
Assistant Examiner—Rebekah A. Griffith
Attorney, Agent, or Firm—Peter C. Richardson; Lawrence C. Akers; Mark Dryer

[57] ABSTRACT

A sensor for determining the partial pressure of carbon dioxide in a liquid, which comprises a carbon dioxide - permeable, liquid and ion-impermeable membrane enveloping an aqueous medium containing an absorber, a fluorescer and a source of bicarbonate ions, which medium exhibits variations in pH as a function of the partial pressure of dissolved carbon dioxide, the ratio of absorber to fluorescer and the characteristics of the absorption spectrum of the absorber and the excitation and emission spectra of the fluorescer being such that the partial pressure of carbon dioxide in the liquid may be determined from the pH of the aqueous medium as measured by the intensity of the fluorescent emission of the fluorescer.

14 Claims, 9 Drawing Sheets

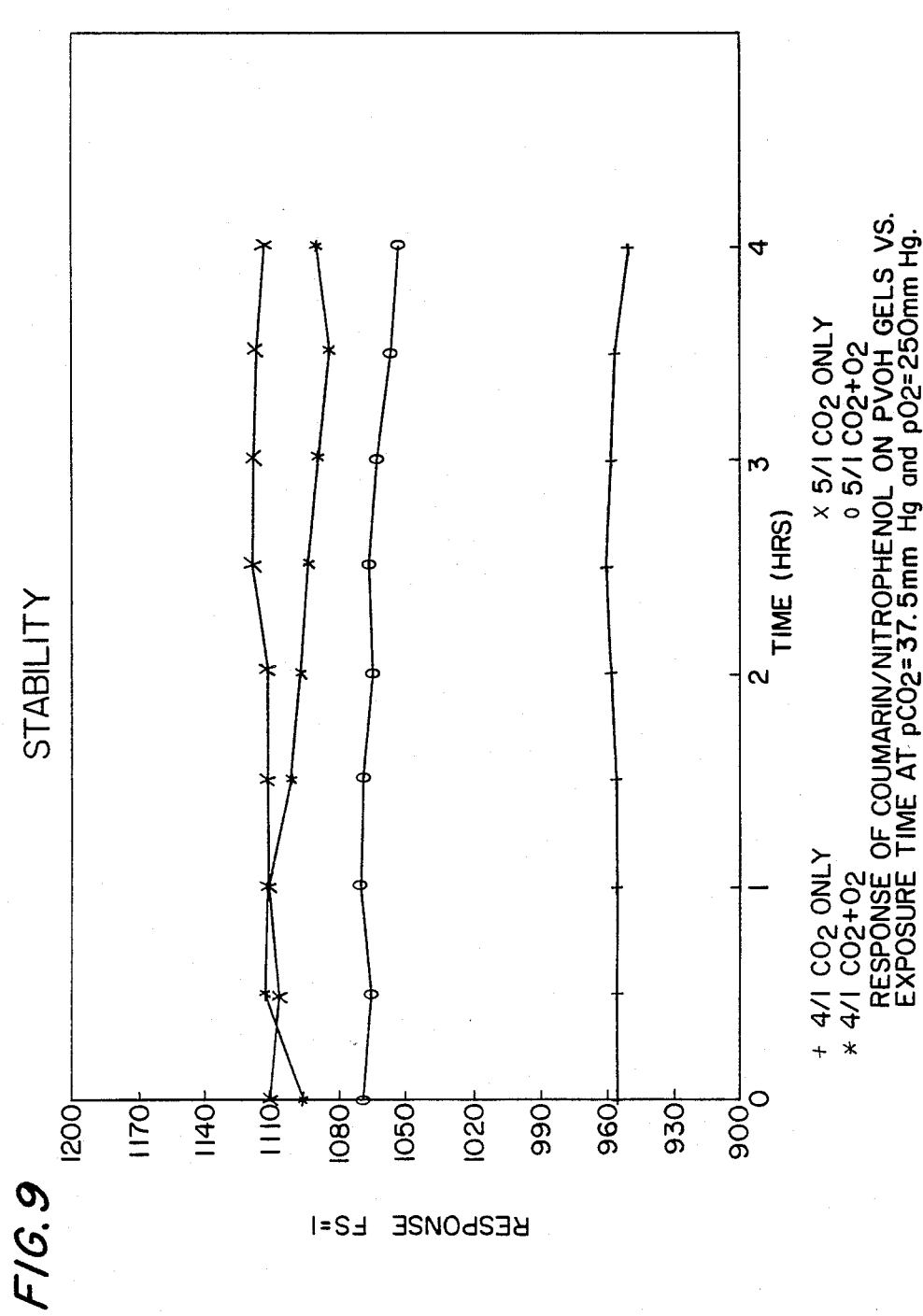

CARBON DIOXIDE SENSOR

BACKGROUND OF THE INVENTION

This invention relates to a carbon dioxide sensor, particularly a sensor for determining the partial pressure of carbon dioxide in a liquid, for example, blood. More particularly, the invention is concerned with a sensor which utilizes the phenomenon known as the "inner filter effect" to modulate the intensity of emission of a fluorescent compound and thereby provide a sensitive and accurate determination of the partial pressure of carbon dioxide in the medium under investigation.

The measurement in blood of pH levels and concentration of gases, particularly oxygen and carbon dioxide, is important during surgical procedures, post-operatively, and during hospitalization under intensive care and numerous devices for the measurement and display of said physiological parameters have been suggested in the art.

U.S. Pat. No. 4,003,707, Lubbers et al., and its reissue Pat. Re No. 31879, disclose a method and an arrangement for measuring the concentration of gases and the pH value of a sample, e.g. blood, involving the use of a fluorescent indicator enveloped by or sealingly embedded in a selectively permeable diffusion membrane. This patent discloses the use of beta-methyl-umbelliferone as a pH indicator.

The use of beta-methyl-umbelliferone as a fluorescent pH indicator was previously disclosed in an article by Raymond F. Chen, Analytical Letters 1[7], 423–428 [1968].

U.S. Pat. No. 4,200,110, Petersen et al discloses the use of a pH sensitive fluorescent indicator in conjunction with a fiber optic pH probe. The fluorescent indicator composition is enclosed within a selectively permeable membrane envelope.

In each of the above prior art references the determination of pH is dependent upon a change of intensity in the fluorescent emission of a suitable indicator. With suitable adjustment of the conditions under which the determination of pH is performed, a pH sensitive fluorescent indicator may be used to measure pCO$_2$.

It has now been found that an improved sensor for determining the partial pressure of carbon dioxide may be based upon the fluorescence "inner filter effect". In such a sensor the emission of an inert fluorescent compound is modulated by the absorption of a pH indicator whose absorption spectrum overlaps the excitation and/or emission spectrum of the fluorescent compound.

The "inner filter effect" is a phenomenon which is known in the art and is described, for example, in "Fluorescence Assay in Biology and Medicine" by Sidney Udenfriend (1962) at pages 108–9. A brief summary of the state of the art relating to absorption-emission optrodes is to be found in an article "Optrodes: Chemically Selective Fiber-Optic Sensors" by S.M. Angel, at pages 38–47 in the April 1987 issue of "Spectroscopy.". This article describes the work of Hirschfeld and others who developed sensors based upon non-radiative energy transfer in which the emission spectrum of the fluorescer overlaps the absorption spectrum of the absorber and absorption occurs without true photon emission and absorption, but rather through a dipole-dipole energy transfer process. Such process is efficient only if the center-to-center molecular distance is less than 70Å since the efficiency falls off as the inverse sixth power of the distance between molecules. In contrast thereto, the sensor of the present invention acts through radiative transfer, as hereinafter described. Notwithstanding the conventional view that radiative energy transfer is less efficient that non-radiative energy transfer, surprisingly it has been found that a viable sensor can be made by following the teachings of the present invention.

U.S. Pat. No. 4,495,293, Shaffar, discloses a fluorometric assay method involving the use of a fluorescer and a reagent system which changes the transmittive properties of the assay solution in the presence of the ligand under investigation and thereby modulates the intensity of fluorescent emission. The fluorescer-absorber system used in this method is an assay kit which reacts with and is used up by the sample solution.

The present invention provides a re-usable sensor for the selective determination of the partial pressure of carbon dioxide in a liquid.

SUMMARY OF THE INVENTION

In accordance with the present invention there is provided a sensor for determining the partial pressure of carbon dioxide in a liquid, which comprises a carbon dioxide - permeable, liquid and ion-impermeable membrane enveloping an aqueous medium which exhibits variations in pH as a function of the partial pressure of dissolved carbon dioxide, said aqueous medium containing: (i) from $5 \times 10^{-5}$M to $1 \times 10^{-3}$M of an absorber whose absorption spectrum exhibits peaks at wavelengths $\lambda_A$ and $\lambda_B$, the absorbances at $\lambda_A$ and $\lambda_B$ being pH-dependent; (ii) a fluorescer having a fluorescent emission spectrum with a peak at wavelength $\lambda_F$ and an excitation spectrum with a peak at wavelength $\lambda_X$, the intensities at $\lambda_F$ and $\lambda_X$ being pH-independent; and (iii) a source of bicarbonate ions which provides bicarbonate ions in a concentration which maintains the pH of the aqueous medium in the range of maximum response of the absorber; wherein the ratio of fluorescer to absorber is in the range from 0.1:1 to 10:1, and there is sufficient overlap between the peaks at wavelength $\lambda_F$ or $\lambda_X$ of the emission and excitation spectra of the fluorescer and the peaks at wavelength $\lambda_A$ or $\lambda_B$ of the absorption spectrum of the absorber so that the partial pressure of carbon dioxide in the liquid may be determined from the pH of the aqueous medium as measured by the intensity of the fluorescent emission at $\lambda_F$.

Preferably the aqueous medium is a transparent aqueous gel, especially a gel formed with the aid of agarose as a gelling agent.

In a preferred embodiment of the invention the absorber (i) or the fluorescer (ii) or both the absorber and fluorescer is bound to a polymer, for example, poly(vinyl alcohol).

DETAILED DESCRIPTION OF THE INVENTION

The sensor of the invention essentially includes a pH-dependent absorber and a pH-independent fluorescer and it is important that the ratio of absorber to fluorescer is carefully balanced in the aqueous medium to provide a responsive and sensitive system. Thus the concentration of absorber should be such that it responds to changes in pH resulting from the ingress of carbon dioxide through the membrane and is sufficient to provide a measurable modulation of the intensity of the fluorescent emission.

Also the absorption spectrum of the absorber must sufficiently overlap the emission and/or excitation spectrum of the fluorescer to provide the desired intensity modulation.

Particularly preferred embodiments which satisfy the above criteria are:

(i) a sensor in which the absorber is 2,6-dimethyl-4-nitrophenol and the fluorescer is 6,7-dimethoxy-coumarin, and (ii) a sensor in which the absorber is methyl (2-nitro-5-hydroxy)benzoate and the fluorescer is dimethyl (2,2'-bifuran-5,5'-dicarboxylate).

In each of the above systems the ratio of fluorescer to absorber is within the range of 0.1:1 to 10:1, the concentration of absorber in the aqueous medium is from $5 \times 10^{-5}$M to $1 \times 10^{-3}$M and the source of bicarbonate ions is sodium bicarbonate.

Furthermore it has been found that a particularly efficient and stable sensor is obtained if the absorber or fluorescer or both the absorber and fluorescer is bound to a suitable polymer. A particularly preferred polymer for this purpose is poly(vinyl alcohol).

Additionally, the sensor is particularly responsive if the aqueous medium is a transparent aqueous gel. Agarose is particularly preferred as a gelling agent because it has appropriate viscoelastic properties and also because it is chemically inert in substantially all systems contemplated for use of the sensor of the invention. Other gelling agents may be used, for example carboxymethylcellulose, but some are not chemically inert and may cause a pH shift or other complications.

In accordance with the above, a particularly preferred embodiment comprises an absorber, for example, 2,6-dimethyl-4-nitrophenol, and a fluorescer, for example, 6,7-dimethoxy-coumarin, bonded to poly(vinyl alcohol) in an 8mM aqueous solution of sodium bicarbonate and formed into a transparent aqueous gel with 0.7% agarose, said gel being enveloped in a silicone membrane.

A suitable sensor is formed by bonding said gel enveloped by said membrane to the distal end of an optical fibre adapted to transmit electromagnetic radiation of wavelength $\lambda_X$ and to be connected at its proximal end to a signal analyzer for receiving emission fluorescence radiation at wavelength $\lambda_F$.

In the sensor according to the invention the bicarbonate acts as a weak buffer whose purpose is to maintain the pH of the aqueous medium in the most appropriate range for the absorber. The required concentration for the bicarbonate requires a knowledge of the $pCO_2$ range to be covered and the optimum pH range of the absorber; and this concentration may be estimated using the Henderson-Hasselbach equation which may be derived from the following explanation of the chemistry of carbon dioxide in aqueous solution:

$$CO_2 + H_2O \rightleftharpoons H_2CO_3 \rightleftharpoons HCO_3^- + H^+ \qquad (1)$$

therefore dissolution of carbon dioxide in water lowers the pH of the solution.

The pH is related to the dissolved carbon dioxide as follows:

$$K_{H_2CO_3} = \frac{[HCO_3^-][H^+]}{[H_2CO_3]}$$

but from Equation (1) above:

$$[H_2CO_3] = [CO_2] = \alpha pCO_2$$

where $\alpha$ is the solubility factor of carbon dioxide in water.

Thus $K_{H_2CO_3} = \dfrac{[HCO_3^-][H^+]}{\alpha p CO_2}$ or $[H^+] = \dfrac{\alpha p CO_2 \cdot K_{H_2CO_3}}{[HCO_3^-]}$ or $-\log[H^+] = pH = -\log(\alpha p CO_2 \cdot K_{H_2CO_3}) + \log[HCO_3^-]$ therefore $pH = pK_{H_2CO_3} + \log \dfrac{[HCO_3^-]}{\alpha p CO_2} \qquad (2)$ Equation (2) is the Henderson-Hasselbach equation.

In practice, [HCO3—] is ajusted by adding a bicarbonate, preferably sodium bicarbonate, so that the pH of the solution remains in the active range of the pH indicator, i.e. the absorber, over the range of $pCO_2$ which is to be measured.

As discussed above with reference to the background prior art, fluorescence spectometry is a known analytical method for the determination of analytes in solution. However, it is subject to certain types of interference, of example, quenching and the presence of fluorescent impurities.

The present invention takes advantage of the inner filter effect, which occurs when an impurity present in the solution absorbs light intended for excitation of the fluorescer or light emitted by the fluorescer. In either case the intensity of the emitted fluorescent radiation is less than would otherwise be expected.

In the present invention a non-fluorescing pH indicator which absorbs radiation, i.e. an absorber, and whose absorption spectrum overlaps with the excitation and-/or emission spectrum of an appropriate fluorescer is used in combination with said fluorescer whereupon the intensity of the fluorescent emission is modulated by the presence of said absorber. Since the absorption is dependent upon the pH of the solution, the intensity of fluorescence gives a measure of the pH.

BRIEF DESCRIPTION OF THE DRAWINGS

Data relating to the responses of the compounds used in the preferred embodiments of the sensors of the invention are illustrated graphically in the accompanying drawings, in which:

FIG. 9 illustrates stability curves.

Figure 1:
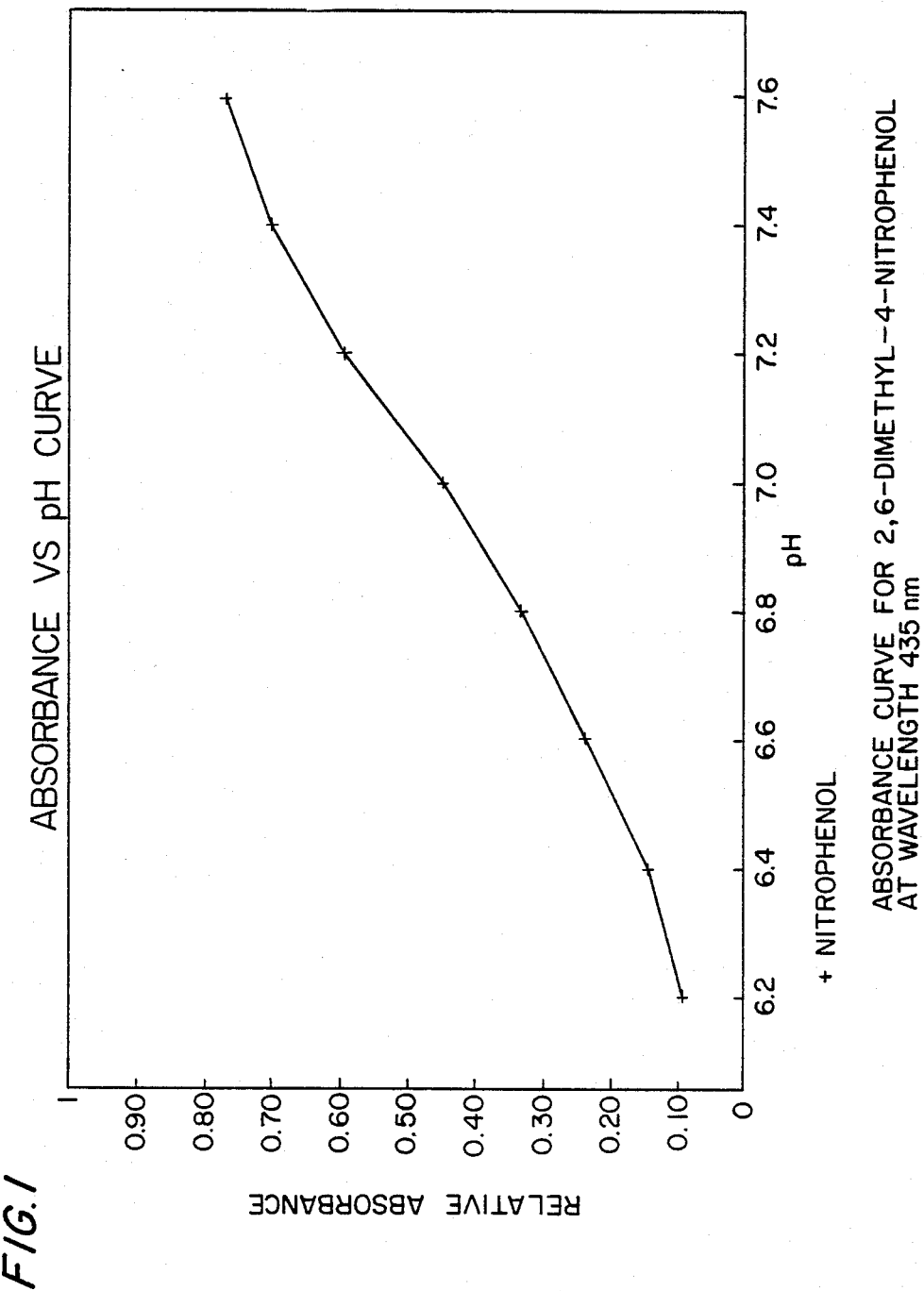
FIG. 1 is an absorbance curve at varying pH levels for the absorber 2,6-dimethyl-4-nitrophenol, at a wavelength of 435 nm.

In the experiments which produced the curves illustrated in the drawings the most extensively studied fluorescer/absorber combination studied was 6,7-dimethoxycoumprin, having the formula:

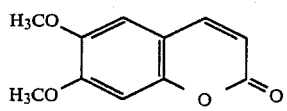

as fluorescer, and 2,6-dimethyl-4-nitrophenol, having the formula:

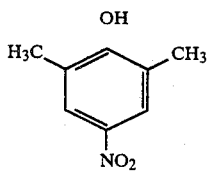

as absorber.

Another preferred combination is dimethyl (2,2'-bifuran-5,5'-dicarboxylate) having the formula:

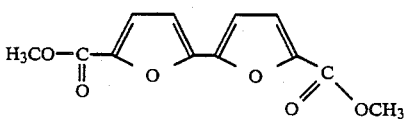

as fluorescer, and methyl (2-nitro-5-hydroxy)-benzoate having the formula:

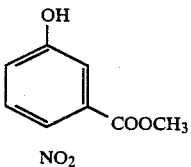

as absorber.

A particularly preferred embodiment of the invention is one wherein the fluorescer and/or absorber is attached to a polymer for the purposes of immobilization and increased water solubility. Where the fluorescer or absorber does not have the appropriate functionality to attach it to a polymer the compound is synthesized with a functionalized chain which can be bound to polymer functional groups. Thus the resulting functionalized fluorescer derived from the coumarin compound of formula I is scopoletin-(5-valeric acid)ether methyl ester having the formula:

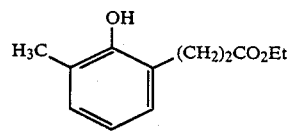

and the functionalized absorber derived from the nitrophenol of formula (II) is 2-methyl-4-nitro-6-(3-propionic acid)phenol ethyl ester having the formula:

$$H_3C \underset{NO_2}{\overset{OH}{\underset{}{\bigcirc}}} (CH_2)_2CO_2Et \qquad (VI)$$

The absorbance curve at a wavelength of 435 nm for 2,6-dimethyl-4-nitrophenol of formula (II) at varying pH levels is shown in FIG. 1. This curve shows that at high pH (low $pCO_2$) the absorbance is high and, consequently, the emitted fluorescence (of the accompanying fluorescer) will be low. At low pH (high $pCO_2$) the converse is true.

In the $pCO_2$ sensor of the present invention the fluorescer and absorber is used in combination with a sodium bicarbonate solution and a carbon-dioxide permeable membrane.

Figure 2:
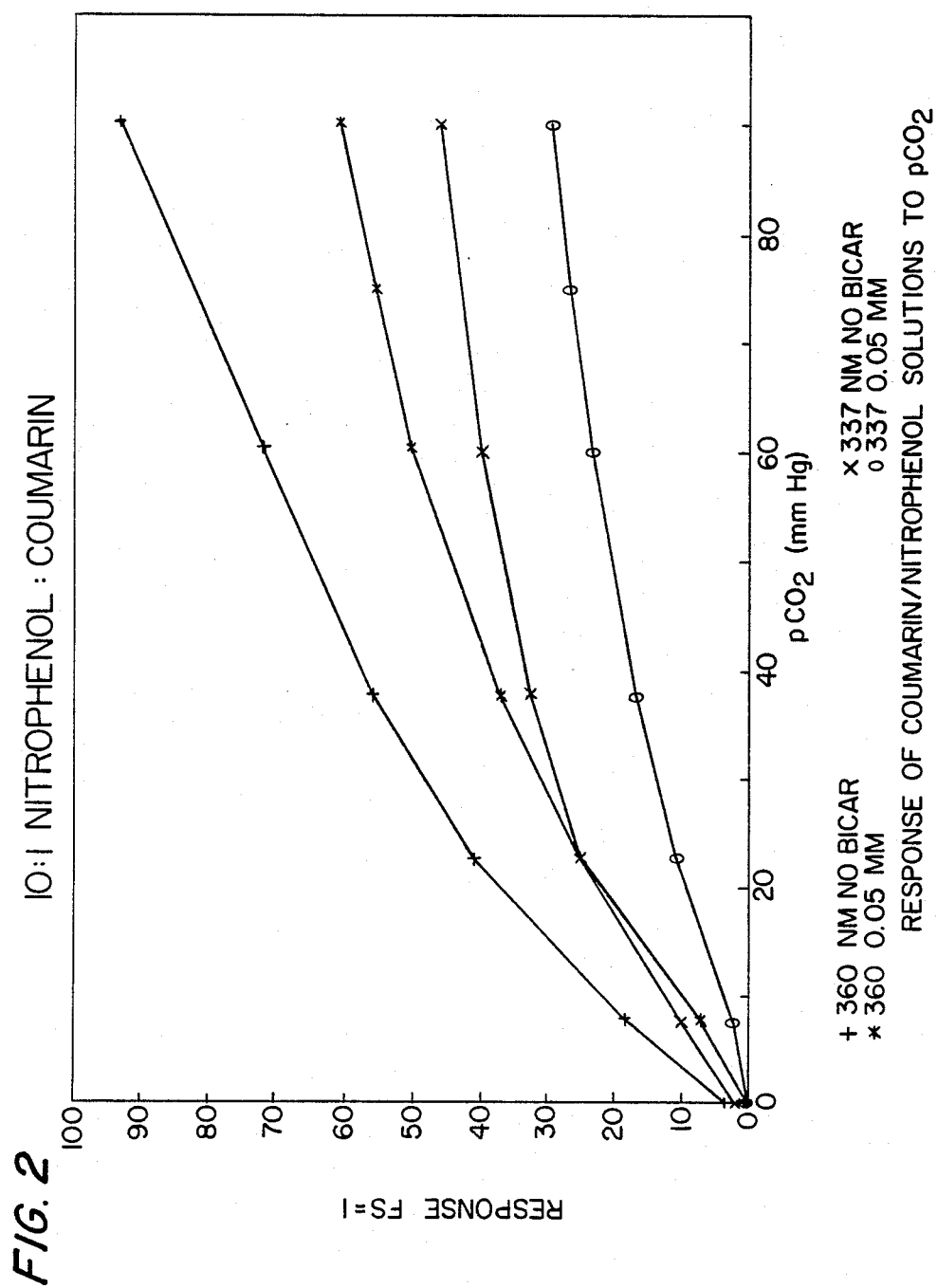
FIG. 2 shows response curves for a 1:10 fluorescer-/absorber system at varying concentrations of carbon dioxide and at two different excitation wavelengths.

FIG. 2 of the accompanying drawings shows the response at an emission wavelength of 435 nm of a solution containing a 1:10 mole ratio of 6,7-dimethoxycoumarin to 2,6-dimethyl-4-nitrophenol at two different excitation wavelengths, 360 nm and 337 nm, and two different bicarbonate concentrations. The fluorescence intensity changed significantly in response to change in $pCO_2$, thus demonstrating the feasibility of the inner filter effect. The presence of bicarbonate in these solutions reduced the response of the system to carbon dioxide. At the concentration used, i.e. $1 \times 10^{-4}$M 6,7-dimethoxycoumarin, addition of even a small amount of bicarbonate raised the pH beyond the optimum value for this fluorescer/absorber system. FIG. 2 also shows that the response at an excitation wavelength of 360 nm is stronger than at an excitation wavelength of 337 nm, due to more intense fluorescence of the 6,7-dimethoxycoumarin when excited at 360 nm.

Figure 3:
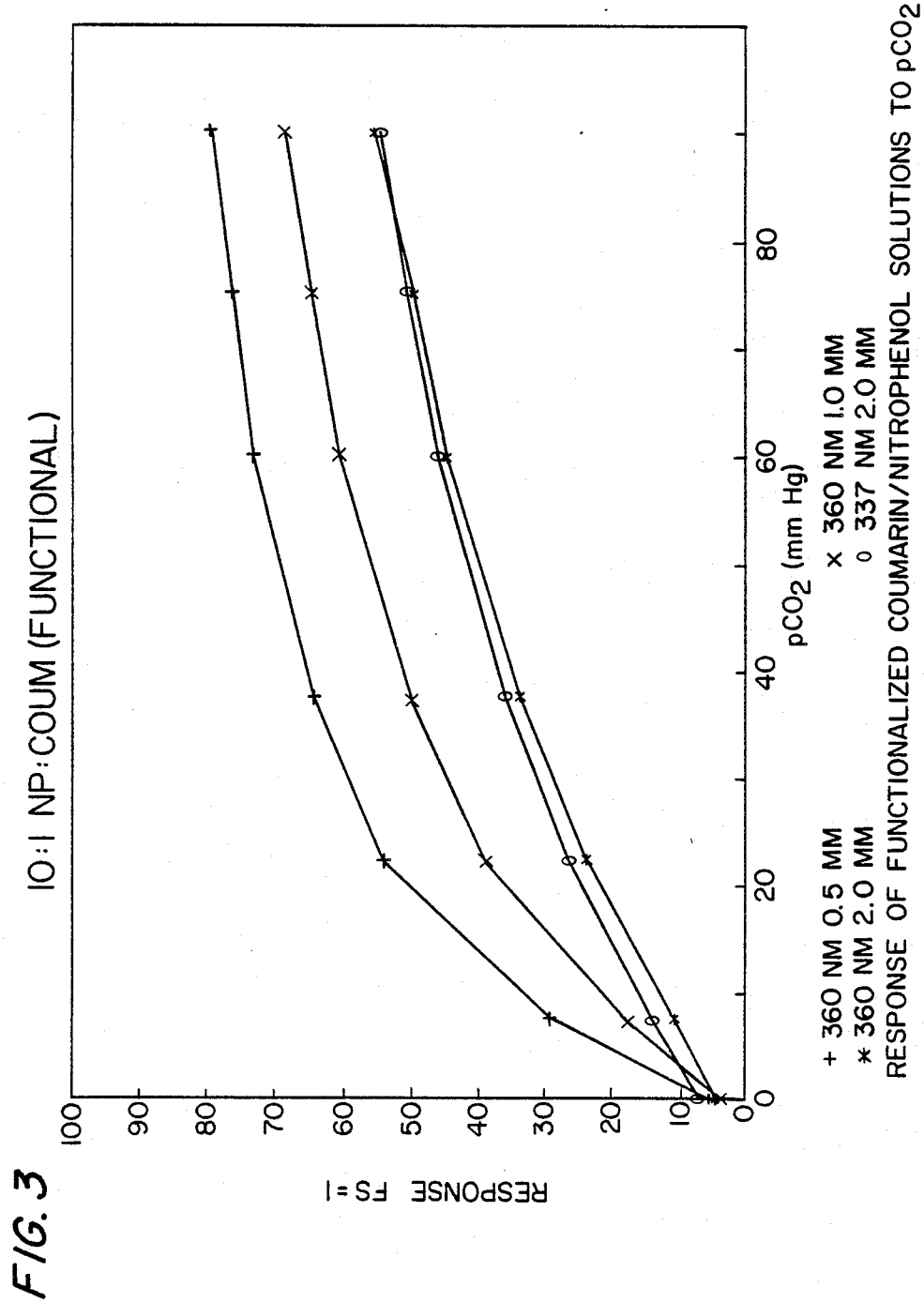
FIG. 3 shows response curves for a system using functionalized fluorescer and absorber as hereinafter described.

FIG. 3 shows the response of a 1:10 solution of the functionalized fluorescer of formula (V) and functionalized absorber of formula (VI) to carbon dioxide. As in the system of FIG. 2, the response decreased with increasing bicarbonate concentration, but at a bicarbonate concentration of 2 mM the difference in response due to excitation wavelength was small.

When the functionalized fluorescer and absorber compounds were bound to poly(vinyl alcohol) by techniques described hereinafter the polymer binding increased the water solubility of the compounds so that it was possible to achieve higher concentrations and also to eliminate the possibility of leaching of the compound through the membrane used in the sensor. The resulting coumarin-polymer complex has the formula

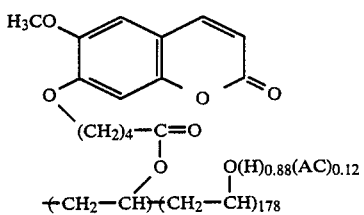

(VII)

and the nitrophenol-polymer complex has the formula:

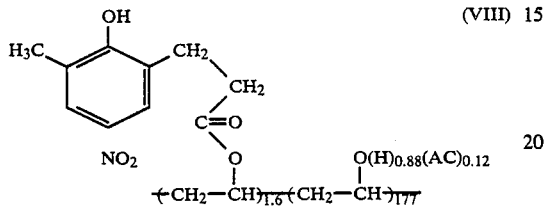

(VIII)

Figure 4:
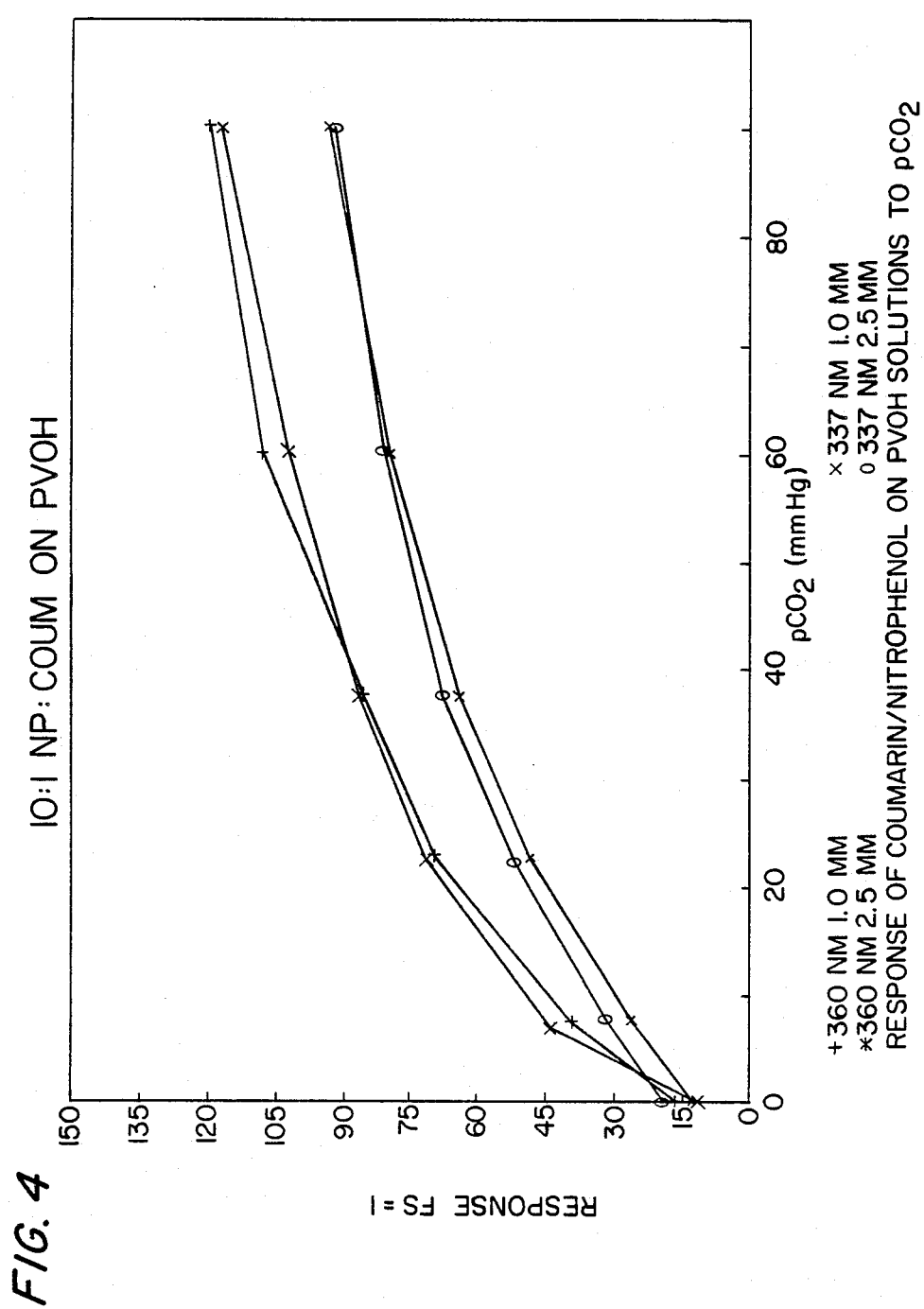
FIG. 4 shows response curves for the fluorescer/absorber system bonded to poly)vinyl alcohol)

FIG. 4 illustrates the response of the above compounds (VII) and (VIII) in solution to carbon dioxide. The response decreased at higher bicarbonate concentration and the reponses at 337 nm and 360 nm excitation were nearly indistinguishable.

The coumarin/nitrophenol polymer system was examined over a variety of ratios, concentrations and bicarbonate levels at an excitation wavelength of 337 nm and an emission wavelength of 435 nm.

The results of these studies are listed in the following Table 1, wherein dynamic range is defined as the fluorescent intensity of the solution at high $pCO_2$ (about 90 mm Hg) minus the intensity at low $pCO_2$ (about 7.5 mm Hg).

TABLE 1

DYNAMIC RANGE DATA FOR COUMARIN/PVOH (FORMULA VII) + NITROPHENOL/PVOH (FORMULA VIII) IN AQUEOUS SOLUTION

| [COUM]/[NP] [$HCO_3^-$],mM | 1.25/1 | 1.0/1 | 0.5/1 | 0.4/1 | 0.2/1 | 0.1/1 | 0.07/1 |
|---|---|---|---|---|---|---|---|
| 0 | 167 | | | 82 | 69 | 30 | 33 |
| 0.5 | | 275 | | | | | |
| 1.0 | 276 | 240 | 180 | 180 | 74 | | |
| 1.5 | | | 170 | | | | |
| 2.0 | | | | 160 | | | |
| 2.5 | | | | | | 61 | |
| 5.0 | | | | | 108 | 24 | 19 |

Figure 5:
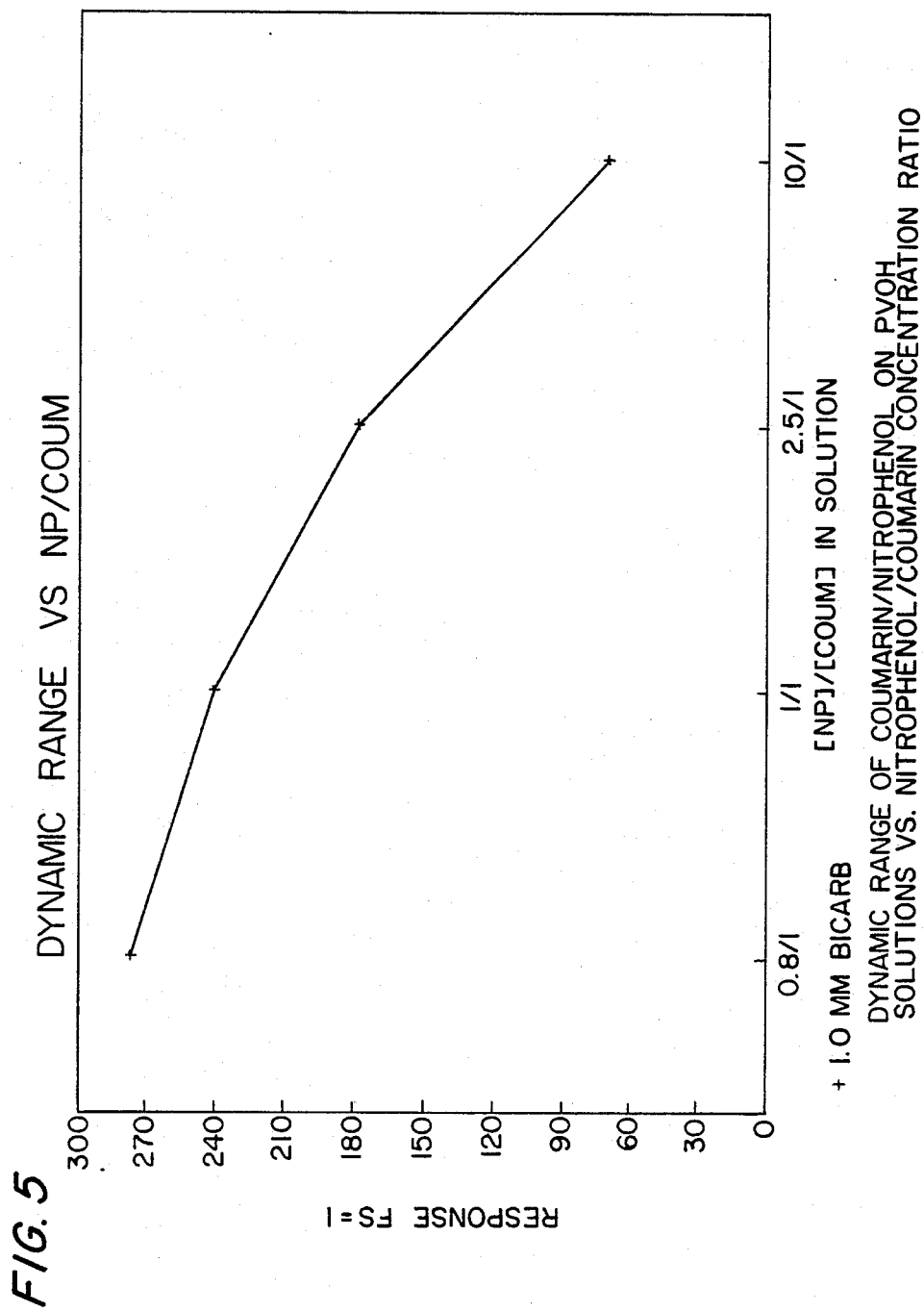
FIG. 5 illustrates dynamic range curves for varying proportions of fluorescer/absorber in solution.

[NP] = $1 \times 10^{-4}$ M
Fixed scale sensitivity = 1.0
Excitation wavelength = 337 nm
Emission wavelength = 435 nm Table 1 indicates that, generally, the response tends to increase with increasing coumarin/nitrophenol ratios. This trend is illustrated in FIG. 5, where representative data from Table 1 are plotted showing the response versus nitrophenol/coumarin ratio at a constant nitrophenol concentration of $1 \times 10^{-4}$ M and a constant bicarbonate concentration of 1.0 mM. The optimum ratio of nitrophenol to coumarin is below 1.0. Although the principal absorption band of the nitrophenol absorber is centered at around 450 nm, and hence partially overlaps the coumarin fluorescer emission at 435 nm, the nitrophenol also exhibits an absorption band near 340 nm. Hence, some of the incident radiation at 337 nm is absorbed by the nitrophenol before it becomes available to excite the coumarin. Therefore the higher the coumarin level (i.e., lower nitrophenol/coumarin ratio), the greater the probability that the incident photons will excite the coumarin before being absorbed by the nitrophenol. This explains the trends shown in Table 1 and FIG. 5.

The concentration of the nitrophenol absorber used in the tests listed in Table 1 is $1 \times 10^{-4}$ M, i.e. within the working range of $5 \times 10^{-5}$ M to $1 \times 10^{-3}$ M of the invention.

The fact that the absorber/fluorescer system of the present invention acts through radiative transfer is demonstrated by calculating the average molecular distance of the compounds in solution. The highest concentration contemplated for the nitrophenol absorber is $1 \times 10^{-3}$ M and the highest concentration contemplated for the coumarin fluorescer is $1 \times 10^{-2}$ M. Since the higher the concentration, the closer the molecule will be in solution, these concentrations represent a "worst case". At these concentrations the molecular distance between the absorber (NP) and fluorescer (COUM) may be calculated as follows:

$$[NP] = 1 \times 10^{-3} M = (1 \times 10^{-3} \text{ moles/l})$$
$$(6 \times 10^{23} \text{ molecules/mole})$$
$$= 6 \times 10^{20} \text{ molecules/l} =$$
$$6 \times 10^{17} \text{ molecules/cm}^3$$

$$\therefore V^{NP}_{effective} = \frac{1}{[NP]} = \frac{1}{6 \times 10^{17}} =$$
$$1.67 \times 10^{-18} \text{ cm}^3/\text{molecule} =$$
$$\frac{4}{3} \pi (R^{NP}_{effective})^3$$

$$\therefore R^{NP}_{effective} = \sqrt[3]{\frac{3(1.67 \times 10^{-18})}{4\pi}} = 7.36 \times 10^{-7} \text{ cm.} = 73.6 \text{Å}$$

$$[COUM] = 1 \times 10^{-2} M = 6 \times 10^{21} \text{ molecules/l} =$$
$$6 \times 10^{18} \text{ molecules/cm}^3$$

$$\therefore V^{COUM}_{effective} = \frac{1}{[COUM]} = \frac{1}{6 \times 10^{18}} =$$
$$1.67 \times 10^{-19} \text{ cm}^3/\text{molecule}$$
$$= \frac{4}{3} \pi (R^{COUM}_{effective})^3$$

$$\therefore R^{COUM}_{effective} = \sqrt[3]{\frac{3(1.67 \times 10^{-19})}{4\pi}} =$$
$$3.42 \times 10^{-7} \text{ cm} = 34.2 \text{Å}$$

$$\therefore D = \text{distance between molecule centers}$$
$$= 73.6 + 34.2$$
$$= 107.8 \text{Å. which is} > 70 \text{Å}$$

Therefore for the said "worst case" the intermolecular distance is too great for radiationless energy transfer to be the dominant effect.

For a more preferred concentration, as used in the solutions of Table 1 above, the intermolecular distances are even greater:

$$[NP] = [COUM] = 1 \times 10^{-4} M = 6 \times 10^{19} \text{ molecules/l}$$
$$= 6 \times 10^{16} \text{ molecules/cm}^3$$

-continued $$V_{\text{effective}} = \frac{1}{6 \times 10^{16}} = 1.67 \times 10^{-17} \text{ cm}^3/\text{molecule}$$

$$= \frac{4\pi}{3} R^3_{\text{effective}}$$

$$\therefore R_{\text{effective}} = \sqrt[3]{\frac{3(1.67 \times 10^{-17})}{4\pi}} = 1.59 \times 10^{-6} \text{ cm}$$

$$= 1.59 \text{Å}$$

$$\therefore D = 318 \text{Å which is} >> 70 \text{Å}$$

Figure 6:
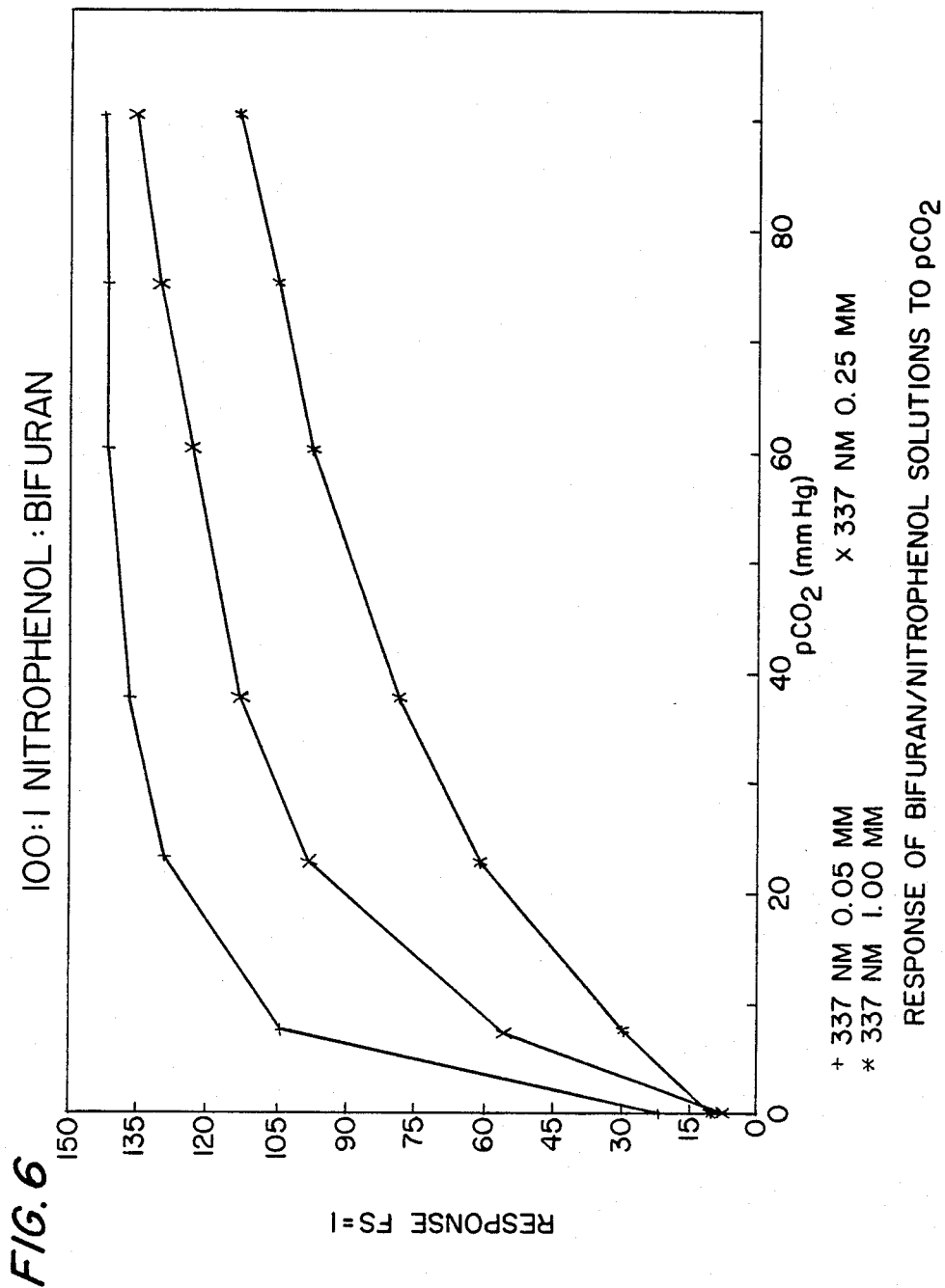
FIG. 6 shows response curves at varying concentrations of carbon dioxide for a fluorescer/absorber system in solution wherein the ratio of fluorescer to absorber is outside the range used in the invention.

The bifuran/nitrophenol pair having formula (III) and (IV), respectively, was also studied in solution. Since the quantum yield of the bifuran was much higher than that of the coumarin, a smaller fluorescer/absorber ratio was required for this pair. The response of a 0.01:1 bifuran nitrophenol solution to $pCO_2$ at an emission wavelength of 390 nm is shown in FIG. 6. This ratio is outside the range used in the invention. As with the other pair, the response decreases with increasing bicarbonate concentration.

When the bifuran fluorescer of formula (III) was bound to poly(ethylene glycol) and the nitrophenol ester absorber of formula (IV) was bound to poly(vinyl alcohol) the bonding of the nitrophenol ester to the polymer produced a shift in the $pK_a$ of this absorber to higher pH values, probably due to steric hindrance and/or hydrogen bonding of the acidic phenol proton to the nearby ester oxygens. Such a shift requires significantly larger concentrations of bicarbonate to bring the pH of the solutions into the range of the $pK_a$ of the absorber for acceptable $pCO_2$ response.

To provide immobility of the absorber/fluorescer system and ease of sensor manufacture, it is desirable that the absorber/fluorescer be in an aqueous gel. The gel may be placed in a sample holder and covered with a carbon dioxide-permeable membrane.

Thus, the formulation, in addition to the appropriate concentrations of absorber and fluorescer, preferably bound to polymers, and bicarbonate, will contain agarose as a gelling agent, preferably in a concentration of 0.7% by weight. The resulting gel is transparent and quite stiff at room temperature.

The gel is prepared by adding aliquots of concentrated stock solutions of fluorescer/poly(vinyl alcohol), absorber/poly(vinyl alcohol) and sodium bicarbonate to a weighed amount of agarose, and diluting to the appropriate volume. In each case the preferred agarose concentration is 0.7% by weight and the preferred nitrophenol absorber concentrations is 1.0 mM. Other concentrations are possible. The resulting gel is heated until homogeneous, then allowed to cool to room temperature.

In a preferred embodiment, the gel is placed in an acrylic sample module, the lower end of which is covered by a carbon dioxide-permeable membrane held in place by a silicone O-ring. The module is placed in an acrylic cuvette where it can be subjected to external illumination and the emission can be detected by a spectrophotometer. Other embodiments are possible.

To evaluate the system, sample gels were warmed to a fluid consistency in a bath at a temperature of 65° C. and then loaded into the sample modules with a disposable pipette. After cooling, the gels were covered with the membrane and examined for bubbles using a stereoscope. If bubbles were detected, the gel was discarded and the module reloaded.

The gels, in the modules, were then equilibrated overnight in a pH 7.4 phosphate-buffered saline solution bath. For dynamic range and sensitivity tests the test gases were then bubbled through the saline bath for 30 minutes, using gas sparger tubes and magnetic stirring, after which the module was transferred immediately to the cuvette in the spectrophotometer. The cuvette also contained pH 7.4 phosphate-buffered saline solution which had been equilibrated with the same test gas. After five minutes additional equilibration of the sample in the cuvette, the bubbling was stopped, and the emission recorded. This procedure was developed so that several modules could be equilibrated in the saline bath simultaneously. For stability tests, all equilibration was performed in the cuvette under constant illumination. The gas bubbling was stopped during measurement of the emission.

Excitation was set at 337 nm using an excitation slit width corresponding to a 10 nm bandwidth. Emission was measured at 435 nm with a 20 nm bandwidth. All data were corrected to a fixed scale sensitivity of 1.0 on a Perkin-Elmer LS-5 spectrophotometer.

For dynamic range and sensitivity, each data point was the average of at least three and as many as six, separate determinations using different samples of the same gel in different modules. Since the stability/selectivity tests did not lend themselves to multiple-sample equilibration, those data represent single measurements.

The following Table 2 shows the results of the dynamic range experiments in which the gels with various coumarin/nitrophenol ratios and bicarbonate levels were exposed to phosphate buffered saline solutions at pH 7.4 and $pCO_2$ equal to 7.5 and 90 mm Hg. The dynamic range data were calculated by subtracting the average measured emission after equilibration at 1% $CO_2$ in $N_2$ ($pCO_2 = 7.5$ mm Hg) from the average emission after equilibration at 12% $CO_2$ in $N_2$ ($pCO_2 = 90$ mm Hg).

TABLE 2

| DYNAMIC RANGE DATA FOR COUMARIN/PVOH + NITROPHENOL/PVOH IN 0.7% AGAROSE GELS | | | | | | | |
|---|---|---|---|---|---|---|---|
| [COUM]/[NP]→ [HCO$_3^-$],mM | 0.6/1 | 1.0/1 | 2.0/1 | 3.0/1 | 4.0/1 | 5.0/1 | 6.0/1 |
| 2 | | | 214 | 187 | 198 | | |
| 5 | 132 | 146 | 204 | 169 | 160 | | |
| 8 | | | 196 | 196 | 240 | 222 | 188 |
| 12 | | | | | 192 | 201 | 178 |
| 15 | | | | | | | 184 |

[NP] = 1 × 10$^{-3}$M
FIXED SCALE SENSITIVITY = 1.0
EXCITATION WAVELENGTH = 337 nm
EMISSION WAVELENGTH = 435 nm

Figure 7:
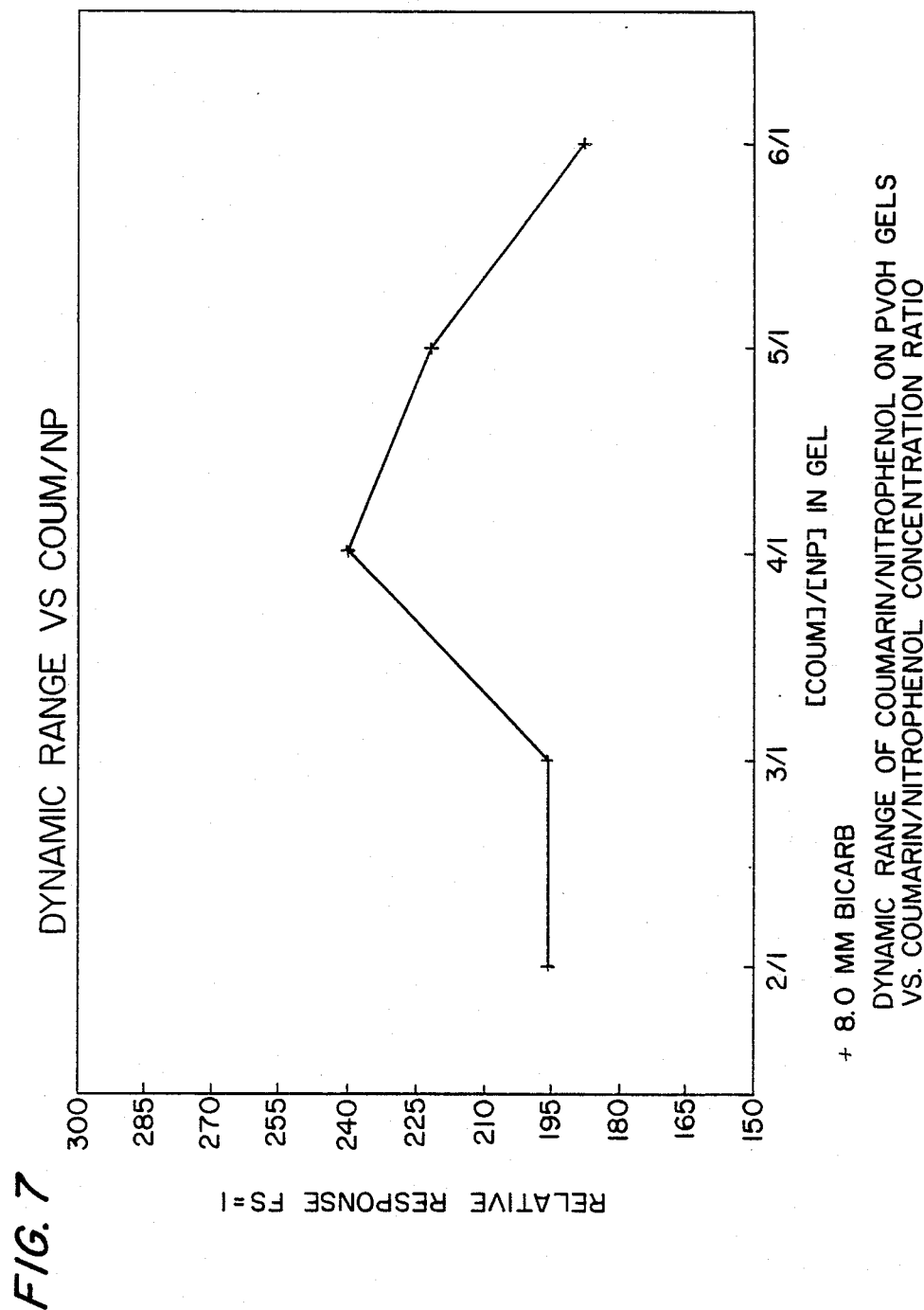
FIG. 7 shows dynamic range curves for varying proportions of fluorescer/absorber on poly(vinyl alcohol) gels.

The data in Table 2 indicate that dynamic range increases with increasing coumarin/nitrophenol ratio up to a ratio of between 2:1 and 5:1 depending upon bicarbonate concentration. This trend is shown graphically in FIG. 7, in which response is plotted against coumarin/nitrophenol at 8 mM bicarbonate concentration.

Compared to the solutions, the gels are relatively insensitive to changes in bicarbonate concentration.

The maximum dynamic range gels were prepared with coumarin/nitrophenol ratios of 4/1 and 5/1 at a bicarbonate concentration of 8 mM, as shown in Table 2. These two gels were then subjected to additional tests to determine their sensitivity to changes in $pCO_2$ and their stability in the absence and presence of oxygen.

For the sensitivity tests, 3% $CO_2$ in $N_2$ ($pCO_2=22.5$ mm Hg), 5% $CO_2$ in $N_2$ ($pCO_2=37.5$ mm Hg), 8% $CO_2$ in $N_2$ ($pCO_2=60$ mm Hg), and 10% $CO_2$ in $N_2$ ($pCO_2=75$ mm Hg) mixtures were used in addition to 1% and 12% $CO_2$ in $N_2$.

Figure 8:
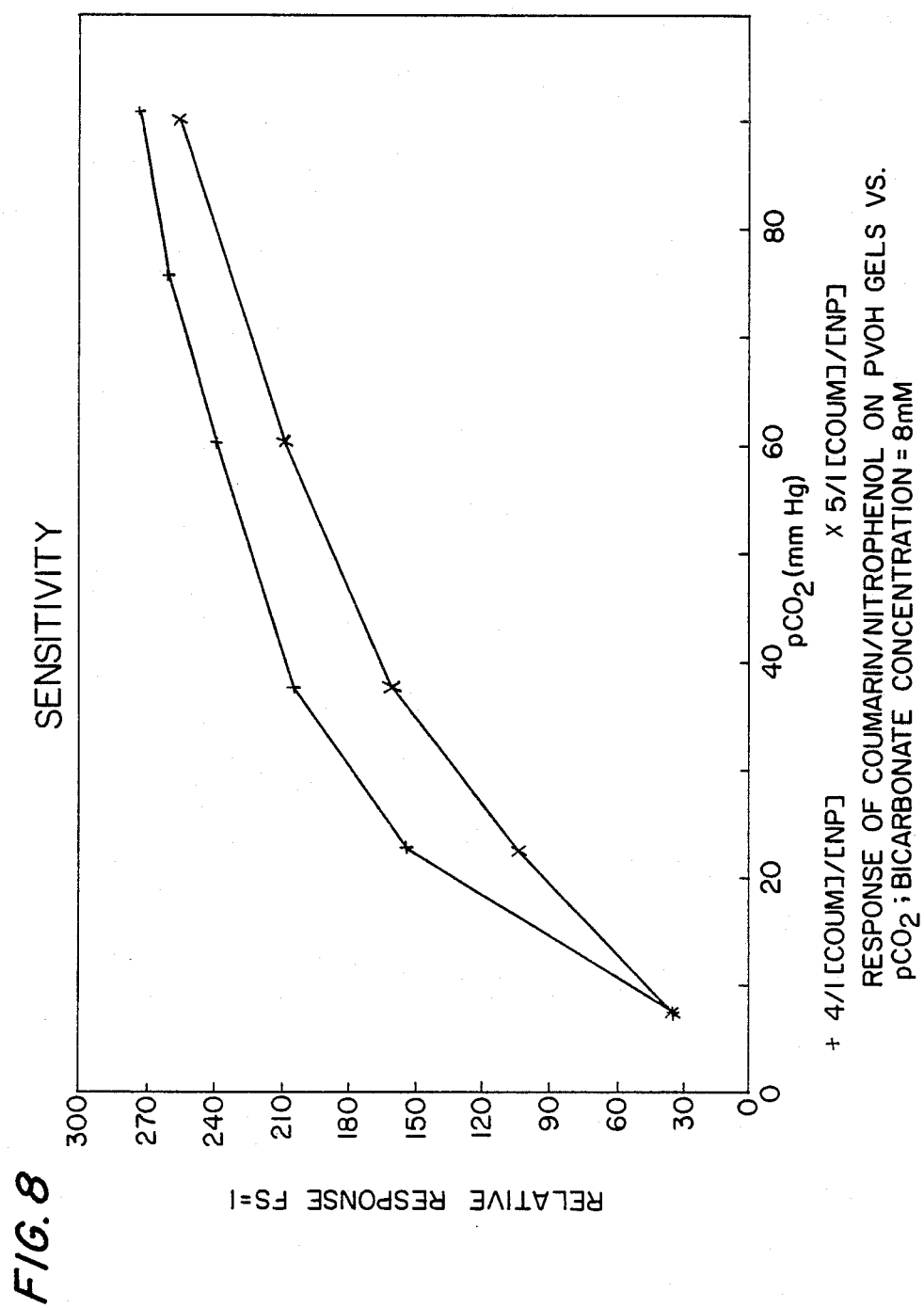
FIG. 8 illustrates sensitivity response curves for varying concentrations of carbon dioxide.

The sensitivity of the gels to changes in $pCO_2$ was determined by measuring the response of the gels to different values of $pCO_2$ in phosphate buffered saline solutions. The results are shown in FIG. 8. For both gels, the sensitivity to small changes in $pCO_2$ was greater at lower values of $pCO_2$, with both curves approaching plateaus at high $pCO_2$. This is because at the pH values present in these gels, the nitrophenol was operating in the lower left portion of the absorbance vs. $pCO_2$ curve shown in FIG. 1. The 4/1 ratio gel exhibited higher sensitivity at very low $pCO_2$ levels, while the sensitivity of both gels was similar above 20-25 mm Hg $pCO_2$.

A test to check the stability of the gels under constant illumination in the fluorescene spectrophotometer, was designed. The gels were illuminated for four hours in phosphate-buffered saline solution equilibrated at a $pCO_2$ of 37.5 mm Hg. Intensity readings were taken at start of the test, and at 30 minute intervals thereafter. The results of this test are shown by the + and X symbols in FIG. 9. The response to both gels was quite flat over most of the period of exposure, with some evidence for a slight decrease in emission after about 3.5-4 hours. The maximum deviations from the mean values were 0.7% for the 4/1 coumarin/nitrophenol gel, and 0.5% for the 5/1 coumarin/nitrophenol gel.

During open-heart surgery the patient's blood is oxygenated. $pO_2$ levels as high as 250 mm Hg are sometimes maintained. The presence of varying oxygen levels is a potential complication for sensors employing fluorescence, since oxygen is known to quench the fluorescence of many organic compounds. In order to test the stability and selectivity of the gels (although these tests are partially dependent upon the selectivity of the membrane as well), stability tests similar to those described above were performed, except that after initial equilibration of the gels at a $pCO_2$ of 37.5 mm Hg, the tests were run using a gas mixture containing 5% $CO_2$ ($pCO_2=37.5$ mm Hg) and 33% $O_2$ ($pO_2=250$ mm Hg). The results are shown by the * and O symbols in FIG. 9. Comparison of these data with the $CO_2$ only data in the same figure indicates a gradual decrease in intensity which is observed after about one hour of illumination. This loss of signal may be the result of either gradual quenching due to slow diffusion and dissolution of oxygen into the gel, or an accelerated rate of photo-decomposition of the compounds in the presence of oxygen. For both gels, the drift was on the order of 1.5% to 2.5% over the 4 hour period.

The following Preparations illustrate the preparation of the poly(vinyl alcohol) - bound scopoletin derivative of formula (VII) and the poly(vinyl alcohol) - bound 4-nitrophenol derivative of formula (VIII) used in the sensors of the invention.

PREPARATION 1

10.05 grams of poly(vinyl alcohol), (PVOH), 85% hydrolyzed and molecular weight of 10,000; 0.501 grams of scopoletin-(5-valeric acid)ethyl methyl ester (SVEME) and 100 cc. dimethyl acetamide (DMAC) were charged to a dried 200 ml flask containing a magnetic stir bar and fitted with a reflux condenser and argon purge. The mixture was heated at 120° C. for 20 hours with stirring in an oil bath. Thin layer chromatography (TLC) of the solution showed mobile and immobile fluorescent spots, about equal intensity. (TLC conditions: silica gel GF, ethyl acetate eluant, SVEME $R_f=$about 0.9) 0.0300 grams of p-toluene sulfonic acid monohydrate (PTSA) was added and the reaction mixture was heated at 110° C., oil bath temperature, for two hours. TLC shows no change. The lot solution was poured into 1 liter of acetone which was magnetically stirred in a beaker. The polymer precipitated as flocs and haze. The flocs settled, and the supernatant was decanted and replaced by fresh acetone. This was repeated 6 times. (The first supernatant was saved for further workup). The washed polymer flocs were filtered by vacuum and the filter cake washed on a fritted glass funnel 3 times with acetone. The filter cake was dried in a vacuum oven at 50°/1 torr. Yield 4.37 grams (41.6%). The first supernatant had about 300 cc methylene chloride added to it with stirring. Colloidally dispersed polymer coagulated and was isolated as described above, giving 4.53 grams. Total yield, 8.90 grams (85%).

The polymers are soluble in water. TLC of the first polymer fraction (water solution) shows no fluorescent spot migration, only a stationary fluorescent spot, indicating that unreacted scopoletin has been completely washed out of the polymer product during workup.

The actual content of combined scopoletin in the isolated PVOH product was determined spectrosopically. A Cary Model 14 UV-vis spectrophotometer was used. The molar extinction coefficient of SVEME in 50% ethanol at 345 nm was determined and found to be $9.40 \times 10^3$ 1./cm.mo. The absorption spectrum of a known weight of polymer production in 50% ethanol was determined and the concentration of scopoletin in the polymer solution found using the molar extinction coefficient of SVEME in the equation $$A = \epsilon c l$$

where  $A$ = Absorbance $\left(= \text{long} \frac{I_o}{T}\right)$ $\epsilon$ = molar extinction coefficient, 1./(cm.mo.)

$C$ = concentration, moles/liter $l$ = light pathlength in sample = 1.00 cm.

The content of SVE bound in PVOH was found to be $5.85 \times 10^{-5}$ moles/gram.

The starting ratio of SVE to PVOH was $$\frac{0.501}{3.06.32/10.05} = 1.63 \times 10^4 \text{ moles/gram}$$

The trans-esterification effectiveness was $$\frac{5.85 \times 10^{-5}}{1.63 \times 10^{-4}} \times 100 = 35.9\%$$

PREPARATION 2

Preparation of Poly(vinyl alcohol)-scopoletin ester (molecular weight 96,000)

10.02 grams of PVOH (96,000 MW), 0.498 grams of SVEME and 170 cc of DMAC were charged to a 200 ml. flask and the same procedure as in Preparation 1 was followed.

The product was isolated by pouring the reaction mixture into 1700 cc. of acetone with stirring, decanting the supernatant several times, vacuum filtering and washing with acetone. Yield after drying was 7.86 g; 75% all from the first precipitation.

The content of SVEME in the polymer product was $2.15 \times 10^{-5}$ moles/gram.

PREPARATION 3

Preparation of Poly(vinyl alcohol)-[2-methyl-4-nitro-6-(3-propionic acid)-phenol]ethyl ester (10,000 MW)

4.017 grams of PVOH, 85% hydrolyzed and molecular weight of 10,000; 0.402 grams of 2-methyl-4-nitro-6-(3-propionic acid)-phenol ethyl ester (NP-1) and 40 cc. DMAC were charged into a 100 cc. flask and the same procedure as in Preparation 1 was followed.

The product was isolated by precipitation in 400 cc. of acetone, washing several times, vacuum filtering and washing with acetone.

Yield, after drying was 3.52 grams; 80%; all from the first precipitation.

The content of NP-1 in the product was $2.09 \times 10^{-4}$ moles/gram.

PREPARATION 4

Preparation of Poly(vinyl alcohol)-NP-1 Ester (96,000 MW)

4.034 grams of PVOH, 86% hydrolyzed, 96,000 MW; 0.4029 grams of NP-1 and 70 cc. DMAC where charged to a 100 cc. flask and the same procedure as in Preparation 1 was followed.

The product was precipitated in 700 cc. acetone.

The yield was 3.89 g., 88%, all from the first precipitation.

The content of NP-1 in the polymer was $1.29 \times 10^{-4}$ moles/gram.

We claim:

1. A sensor for determining the partial pressure of carbon dioxide in a liquid, which comprises a carbon dioxide permeable, liquid and ion impermeable membrane enveloping a transparent aqueous gel which exhibits variations in pH as a function of the partial pressure of dissolved carbon dioxide, said aqueous gel containing: (i) from $5 \times 10^{-5}$M to $1 \times 10^{-3}$M of an absorber whose absorption spectrum exhibits peaks at wavelengths $\lambda_A$ and $\lambda_B$ and whose absorbances at $\lambda_A$ and $\lambda_B$ are pH-dependent; (ii) a fluorescer having a fluorescent emission spectrum with a peak at wavelength $\lambda_F$ and an excitation spectrum with a peak at wavelength $\lambda_X$ and whose fluorscent intensities at $\lambda_F$ and $\lambda_X$ are pH-independent; and (iii) a source of bicarbonate ions which provides bicarbonate ions in a concentration which maintains the pH of the aqueous gel in the range of maximum response of the absorber; wherein the ratio of fluorescer to absorber is in the range from 0.4:1 to 10:1, and there is sufficient overlap between the peaks at wavelength $\lambda_F$ or $\lambda_X$ of the emission and excitation spectra of the fluorescer and the peaks at wavelength $\lambda_A$ or $\lambda_B$ of the absorption spectrum of the absorber so that the partial pressure of carbon dioxide in the liquid may be determined from the pH of the aqueous gel as measured by the intensity of fluorescent emission at $\lambda_F$.

2. A sensor according to claim 1, in which said gel includes agarose as a gelling agent.

3. A sensor according to claim 1, in which the absorber or fluorescer or both the absorber and fluorescer is bound to a polymer.

4. A sensor according to claim 3, in which said ploymer is poly(vinyl alcohol).

5. A sensor according to claim 1, in which the absorber is 2,6-dimethyl-4-nitrophenol, the fluorescer is 6,7-dimethoxy-coumarin and the source of bicarbonate ions is sodium bicarbonate.

6. A sensor according to claim 1, in which the absorber is methyl(2-nitro-5-hydroxy) benzoate, the fluorescer is dimethyl (2,2'-bifuran-5,5'-dicarboxylate) and the source of bicarbonate ions is sodium bicarbonate.

7. A sensor according to claim 1, in which said absorber and fluorescer are bonded to polyvinyl alcohol in an 8 mM aqueous solution of sodium bicarbonate which is included in said transparent aqueous gel along with 0.7% agarose as a gelling agent, wherein said membrane is a silicone membrane.

8. A sensor according to claim 7, further including an optical fiber having a distal end and a proximal end and wherein said gel enveloped by said membrane is bonded to the distal end of the optical fiber which is capable of transmitting electromagnetic radiation of wavelength $\lambda_X$ and wherein the proximal end of the optical fiber is connected to a signal analyzer for receiving emission fluorescence radiation at wavelength $\lambda_F$.

9. A sensor for determining the partial pressure of carbon dioxide in a liquid, which comprises a carbon dioxide-permeable, liquid and ion-impermeable membrane enveloping an aqueous medium which exhibits variations in pH as a function of the partial pressure of dissolved carbon dioxide, said aqueous medium containing: (i) from $5 \times 10^{-5}$M to $1 \times 10^{-3}$M of an absorber whose absorption spectrum exhibits peaks at wavelengths $\lambda_A$ and $\lambda_B$ and whose absorbances at $\lambda_A$ and $\lambda_B$ are pH-dependent; (ii) fluorescer having a fluorescent emission spectrum with a peak at wavelength $\lambda_F$ and an excitation spectrum with a peak at wavelength $\lambda_X$ and whose fluorescence intensities at 80 $_F$ and $\lambda_X$ are pH-independent; and (iii) a source of bicarbonate ions which provides bicarbonate ions in a concentration which maintains the pH of the aqueous medium in the range of maximum response of the absorber; wherein said absorber or fluorescer or both said absorber and fluorescer is bound to a polymer and the ratio of fluorescer to absorber is in the range from 0.4:1 to 10:1, and there is sufficient overlap between the peaks at wavelength $\lambda_F$ or $\lambda_X$ of the emission and excitation spectra of the fluorescer and the peaks at wavelength $\lambda_A$ or $\lambda_B$ of the absorption spectrum of the absorber so that the partial pressure of carbon dioxide in the liquid may be determined from the pH of the aqueous medium as measured by the intensity of fluorescent emission at $\lambda_F$.

10. A sensor according to claim 9, in which said polymer is poly(vinyl alcohol).

11. A sensor according to claim 9, in which said absorber is 2,6-dimethyl-4-nitrophenol, said fluorescer is 6,7-dimethoxy-coumarin and said source of bicarbonate ions is sodium bicarbonate.

12. A sensor according to claim 9, in which said absorber is methyl (2-nitro-5-hydroxy) benzoate, said fluorescer is dimethyl (2,2'-bifuran -5,5'-dicarboxylate) and said source of bicarbonate ions is sodium bicarbonate.

13. A sensor for determining the partial pressure of carbon dioxide in a liquid, which comprises a carbon dioxide-permeable, liquid and ion inpermeable membrane enveloping an aqueous medium which exhibits variations in pH as a function of the partial pressure of dissolved carbon dioxide, said aqueous medium containing: (ii) from $5 \times 10^{-5}$M to $1 \times 10^{-3}$M of an absorber whose absorption spectrum exhibits peaks at wavelengths $\lambda_A$ and $\lambda_B$ and whose absorbances at $\lambda_A$ and $\lambda_B$ are pH-dependent, said absorber being selected from the group consisting of 2,6-dimethyl-4-nitrophenol and methyl (2-nitro-5-hydroxy) benzoate; (ii) a fluorescer having a fluorescent emmission spectrum with a peak at wavelength $\lambda_F$ and an excitation spectrum with a peak at wavelength $\lambda_X$ and whose fluoresence intensities at $\lambda_F$ and $\lambda_X$ are pH-independent, said fluorescer being 6,7-dimethoxycoumarin when said absorber is 2,6-dimethyl-4-nitrophenol and said fluorescer being dimethyl (2,2'-bifuran-5,5'-dicarboxylate) when said absorber is methyl (2-nitro-5-hydroxy) benzoate; and (iii) a source of bicarbonate ions which provides bicarbonate ions in a concentration which maintains the pH of the aqueous medium in the range of maximum response of the absorber; wherein the ratio of fluorescer to absorber is in the range from 0.4:1 to 10:1, and there is sufficient overlap between the peaks at wavelength $\lambda_F$ or $\lambda_X$ of the emission and excitation spectra of the fluorescer and the peaks at wavelength $\lambda_A$ or $\lambda_B$ of the absorption spectrum of the absorber so that the partial pressure of carbon dioxide in the liquid may be determined from the pH of the aqueous medium as measured by the intensity of fluorescent emission at $\lambda_F$.

14. A sensor according to claim 13, in which said source of bicarbonate ions is sodium bicarbonate.

* * * * *